United States Patent [19]

Coker et al.

[11] 4,447,532

[45] May 8, 1984

[54] PROCESS FOR THE MANUFACTURE OF LOW D.E. MALTODEXTRINS

[75] Inventors: Lowell E. Coker, Keokuk, Iowa; Kalyanasundram Venkatasubramanian, New Brunswick, N.J.

[73] Assignee: H. J. Heinz Company, Pittsburgh, Pa.

[21] Appl. No.: 373,220

[22] Filed: Apr. 29, 1982

[51] Int. Cl.$^3$ .............................................. C12P 19/14
[52] U.S. Cl. ...................................... 435/99; 127/29
[58] Field of Search ............................ 127/29; 435/99

[56] References Cited

U.S. PATENT DOCUMENTS

| | | | |
|---|---|---|---|
| 2,683,682 | 7/1954 | Miller | 435/184 |
| 3,663,369 | 5/1972 | Morehouse | 435/99 |
| 3,849,194 | 11/1974 | Armbruster | 435/99 X |
| 3,853,706 | 12/1974 | Armbruster | 435/99 |
| 3,912,590 | 10/1975 | Slott | 435/99 |
| 3,974,034 | 8/1976 | Horn | 435/99 |
| 4,062,728 | 12/1977 | Blanchard | 435/99 |
| 4,298,400 | 11/1981 | Armbruster | 435/99 X |

*Primary Examiner*—Sidney Marantz
*Attorney, Agent, or Firm*—Paul & Paul

[57] ABSTRACT

A process for the production of a low D.E. maltodextrin product having a bland non-sweet taste which includes the steps of (1) cooking non-waxy starch in the presence of alpha-amylase to gelatinize and liquefy the starch, (2) dextrinizing the liquefied starch hydrolyzate with alpha-amylase at a temperature above about 93° C. until a D.E. within the range of 10–13 is obtained, (3) stopping the dextrinization reaction by the addition of sufficient mineral acid to inactivate the enzyme within about 30–60 minutes while maintaining the hydrolyzate temperature at least above about 93° C., and then (4) refining the low D.E. maltodextrin while maintaining the hydrolyzate at a temperature of at least above 76° C. until a dry product is obtained. The dry product is preferably produced by spray drying.

3 Claims, No Drawings

PROCESS FOR THE MANUFACTURE OF LOW D.E. MALTODEXTRINS

FIELD OF THE INVENTION

This invention relates to an improved process for the production of low D.E. maltodextrins by the enzymatic hydrolysis of regular corn starch wherein the reaction conditions are controlled to minimize the retrogradation of the starch hydrolyzate during the hydrolysis and refining process steps.

DESCRIPTION OF THE PRIOR ART

There is a large potential market for syrups and syrup solids with bland taste, low sweetness and low hygroscopicity at a low D.E. level. Such hydrolysates and syrup solids are useful as bases for the preparation of food items as well as for bodying agents and as additives having non-sweet, water-holding, non hygroscopic characteristics. Other applications include use as a carrier for synthetic sweeteners, as a flavor enhancer, as an additive for coloring agents, as a spray drying adjunct for coffee extracts or tea extracts, as a bulking, bodying or dispersing agent in synthetic creams or coffee whiteners, as a moisture holding agent in breads, pastries, meats and as a bodying and smoothing agent in puddings, soups and frozen desserts.

In general, prior art teachings for the manufacture of maltodextrins are characterized by the use of acid or acid-enzyme techniques for the hydrolysis of starch.

The applicability and use of low D.E. products and particularly products having a D.E. value of less than about 18 has been limited because of certain significant difficulties inherent in their production. Low conversion starch hydrolyzates which have been produced by methods heretofore known in the art are generally found to be non-uniform, i.e., containing significant quantities of native or unconverted starch that contributes to an undesirable starchy flavor and that has a tendency to retrograde with concomitant haze formation. Furthermore, such products may not be completely soluble and may, through deliquescence, become sticky as well as providing greater sweetening than is desired for many applications. The difficulties encountered in producing low conversion products by known methods as well as the poor properties of such products can possibly be attributed to certain inherent characteristics of the starch granules and also deficiencies in the known hydrolysis methods.

Starch is a naturally occurring polymer of alpha-D-glucose connected by acetal linkages. The acetal linkages are susceptible to both acid and enzyme hydrolysis and both catalysts are employed in preparing starch hydrolyzates. The acid hydrolysis of starch has been shown to be a random process and at a given time an acid hydrolyzed starch product comprises a mixture of many different molecular species which may range from the monomer glucose all the way up to polymers approaching the size of starch. Because of the wide range of molecular sizes obtained in acid hydrolysis it is customary to conduct the conversion to an extent that the long polymers will no longer react with iodine. Accordingly, acid hydrolysis is not well suited for making a low D.E. product, i.e., one having a D.E. value below about 30. Although the degree of hydrolysis can be reduced to obtain lower D.E. products the long polymers present in such products cause rapid retrogradation with an accompanying loss of solubility and clarity. Another disadvantage of hydrolyzing starch with acid is that significant amonts of glucose are always present in the product even when the degree of conversion is held to a low level. Because of the presence of glucose and other low molecular weight saccharides, even low D.E. acid-hydrolyzed products tend to be hygroscopic, sticky, and provide a sweetening effect greater than is desired for many applications.

The use of enzymes for hydrolyzing starch has gained widespread application in recent years and enzymes are employed commercially for manufacturing certain products. Enzymes have an advantage over acid catalysts in that they exhibit specificity for certain linkages. One type of microbial enzyme which is commonly employed is alpha-amylase. Alpha-amylase has the property of splitting 1-4 linkages more or less at random throughout the starch molecule linkages. Moreover, alpha-amylase does not readily hydrolyze the 1-4 linkages in maltose and maltotriose. Thus, it has been reported that when substantially complete conversion of starch is effected with alpha-amylase, maltose and small amounts of trisaccharides and other lower molecular weight polysaccharides, especially those containing the 1-6 linkages, are present in the final hydrolyzate.

Another factor having bearing on the properties of starch hydrolyzates prepared by either acid or enzyme hydrolysis is the manner in which the starch is gelatinized when heated in water. The molecules of native starch are closely bound in the starch granule to a varying degree and those that are closely bound are not particularly susceptible to the action of enzymes. It is not until the starch molecules have been dispersed by swelling and gelatinization in water that significant hydrolytic cleavage will take place. In a conversion procedure where the starch is heated slowly the molecules which are closely bound are dispersed or gelatinized more slowly and therefore are available for attack by the acid or enzymes at much lower rate. The result of this non-uniform rate of gelatinization is that by the time that all of the resistant molecules have been made available for attack the more easily dispersed molecules will already have reduced to a relatively small molecular size range. When the product desired is a regular or high D.E. product the non-uniform degradation of starch is not a serious problem. However, when preparing a low D.E. hydrolyzate product the non-uniformity of gelatinization is particularly undesirable because a high proportion of very large molecules including some intact starch molecules will still be present when the desired low D.E. level is reached.

Another undesirable characteristic of low D.E. starch hydrolyzates prioduced heretofore by known methods, which is related to the non-uniformity of degradation, is the tendency for certain of the larger linear molecules to reassociate with other molecular fragments of starch to form large relatively insoluble aggregates. The rate and extent to which linear starch molecules reassociate into insoluble aggregates is a function of chain length since below a certain length the aggregational tendency is not great. The occurrence of reassociation in a liquid hydrolyzate is evidenced by the appearance of haze and/or a change to a gel or paste having poor solubility in cold water.

Although the reassociation or retrogradation of starch hydrolyzates occurs primarily in cooled hydrolyzates where it is especially objectionable it may occur to a slight extent during the cooking process if the rate of heating is slow. When this happens these molecular aggregates tend to remain intact during subsequent processing and add to the difficulty of filtering the hydrolyzate. The presence of a small amount of native or undegraded starch effectively precludes practical filtration procedures. Since the relative amount of residual starch is larger when limited starch conversion is effected in the case of low D.E. products, the filtration problem is more acute with these products. Any significant amount of retrogradation and its attendant production of insoluble reassociated fragments increases the filtration difficulty. Since filtration is one prerequisite for the production of an acceptable starch hydrolyzate food product (i.e. one that is substantially soluble and uniform in appearance, etc.) the difficulty in filtering low D.E. hydrolyzates has been one of the major obstacles to commercialization of low D.E. starch hydrolyzate products.

Due to the nature of the starch structure, it has been difficult to manufacture a maltodextrin having a low D.E. within the range of about 10-13 from regular corn starch. Such products are often difficult to filter and refine to acceptable standards. In contrast, maltodextrins characterized by a D.E. within the range of about 10-13 can be manufactured from waxy maize starch without filtration and refinery problems. This is most probably the result of the differences in the structure of waxy maize and regular starch. An example of a process for obtaining low D.E. maltodextrins from regular starch is given in U.S. Pat. No. 3,663,369. An example of a process for obtaining low D.E. maltodextrins from waxy maize starch is given in U.S. Pat. No. 3,849,194.

It is an object of this invention to provide methods for the manufacture of maltodextrins characterized by a D.E. of 10-13 from regular corn starch wherein the hydrolyzed product is filterable and free of haze or cloudiness during and after the refining process.

It has been found that maltodextrins within the desirable D.E. range of about 10-13 can be produced from regular corn starch without the previously encountered problems of filterability and handling during the refining process. Maltodextrins within this narrow D.E. range have optimum properties for incorporation in foods. They have the desirable bland, non-sweet, water-holding and non-hygroscopic characteristics, but at the same time have no starch taste and can be formed as free flowing dry powders. In accordance with a preferred embodiment of the process of this invention, regular corn starch is cooked in the presence of an alpha-amylase to gelatinize and liquefy the starch. The liquefied hydrolyzate is then dextrinized with the residual alpha amylase at a temperature above about 93° C. for sufficient time to accomplish the desired D.E. level. When the desired D.E. level is attained, the reaction is stopped by the addition of sufficient mineral acid to lower the pH of the hydrolyzate to a level at which the residual enzyme is inactivated within the time period of from about 30-60 minutes while maintaining a hydrolyzate temperature at least above about 93° C.

The resulting hydrolyzate is then refined by treatment with activated carbon while maintaining the hydrolyzate temperature at least above about 76° C. The filtered hydrolyzate is then evaporated. The evaporated liquor is maintained at a temperature of at least above 76° C. and then spray-dried to produce a free-flowing starch hydrolyzate characterized by a D.E. of 10-13.

While the hydrolyzate after evaporation may be spray dried at percentage dry substance within the range of from about thirty to about eighty percent it is preferred that the evaporation be carried out to produce a dry substance percentage within the range of from about fifty to fifty-five percent.

EXAMPLE 1

Approximately 24,000 gallons of regular corn starch at about 24% dry solids concentration was adjusted to pH 7.0 with caustic-soda. Termamyl 60 brand of alpha-amylase was added at a level of about 0.4% of the weight of the starch. The enzyme containing starch slurry was cooked at a temperature of 104°-107° C. for about 11 minutes and then cooled to 93°-96° C. At this point, the D.E. of the starch hydrolyzate was about 4.2-4.6; the hydrolyzate was translucent and began to show a mud break. The hydrolysis of the starch was continued at a temperature of at least above 93° C. until the D.E. of the hydrolyzate was 10.5. During the course of the hydrolysis reaction at a temperature of at least above 93° C., the rate of the D.E. increase was controlled by retarding the reaction rate by maintaining the pH of the reaction mixture on the low side of the optimum pH for the alpha-amylase chosen, in this particular case between pH 5.0-5.5. When the desired 10.5 D.E. was obtained, the pH of the reaction mixture was lowered to pH 3.3-3.5 by the addition of hydrochloric acid and held 45 minutes to inactivate the enzyme and stop the reaction. During this period, the temperature of the reaction mixture was maintained at least about 93° C. by the injection of steam to retard the tendency of certain hydrolyzate products to aggregate or retrograde. This material filtered at a rate of 100-125 ml per minute through Whatman No. 615 paper. The pH of the material was adjusted to pH 5.5 with soda ash, and activated carbon was added, to decolorize the hydrolyzate. The material was then filtered to remove carbon and other particulate material. The filtrate was then evaporated to about 46% by dry substance and spray-dried to produce a white free flowing powder of 10.5 DE. During the refining operation, the liquid product was maintained at a temperature of at least above 76° C. Filtration rates were good averaging 160-170 gpm. The analysis of the finished product is given in Table 1.

TABLE 1

| ANALYSIS OF MALTODEXTRIN FROM EXAMPLE 1 | |
|---|---|
| Percent Moisture | 3.35 |
| D.E. | 10.5 |
| pH | 4.3 |
| Loose Bulk Density (lbs./ft$^3$) | 28.7 |
| Packed Bulk Density (lbs./ft$^3$) | 36.8 |
| Carbohydrate Composition | |
| Monosaccharides | 1.9 |
| Disaccharides | 2.8 |
| Trisaccharides | 3.2 |
| Tetrasaccharides & Higher | 92.1 |
| Screen Analysis (avg. percent) | |
| on 40 | 0.0 |
| on 100 | 0.2 |
| on 200 | 19.0 |
| through 200 | 79.0 |
| Viscosity (cp) of 40% solution, 80° F. | 92 |
| Flavor | Bland |

COMPARATIVE EXAMPLE 2

Approximately 23,000 gallons of regular corn starch at about 21.7% dry solids concentration was adjusted to pH 7.0 with caustic soda. Termamyl 60 brand of alpha-amylase was added at a level of about 0.5% of the weight of starch. The enzyme containing starch slurry was cooked at a temperature of about 97°–98° C. for about 8 minutes. The cooked slurry was cloudy and did not show a mud break. The cooked slurry was about 6.7 D.E. at a pH of 6.3–6.5. The hydrolysis of the cooked slurry was continued by use of the enzyme at 88°–90° C. without application of external heat. Hydrochloric acid was added to maintain a reaction pH of 5.8–6.0 to retard the rate of D.E. rise. When the D.E. of the hydrolyzate had reached 13.0 D.E., the reaction was stopped by adjusting the hydrolyzate to pH 4.0 with hydrochloric acid. Activated carbon was added and the hydrolyzate was filtered, evaporated to about 46% dry substance and spray dried to produce a white free flowing powder of 14.9 D.E. During the refining operations, external heat was not applied and the hydrolyzate cooled to 68°–71° C. During refining, filtration was poor with rates of the order of 45–55 gpm. Product recovery was poor due to losses during filtration.

Example 2 is illustrative of the poor results obtained when low cooking temperatures, low processing temperatures, poor control of hydrolyzate reaction pH, and improper termination of the hydrolysis reaction exist. It is believed that the product D.E. was high due to failure to maintain control of the rate of rise during the hydrolysis and failure to completely inactivate the alpha amylase when the desired D.E. level had been obtained.

In contrast, Example 1 is illustrative of a set of process conditions to produce regular starch hydrolyzates characterized by a D.E. of 10–13 and good filterability. These products can be successfully produced under a range of process operating conditions, as follows.

| Operating Conditions | Range |
| --- | --- |
| Dry substance of starch slurry | about 17–37% |
| pH of starch slurry during cooking to liquefaction | 6–7 |
| Concentration of alpha amylase | 1.0–0.5% of starch (dry weight) |
| pH range during hydrolysis to maintain D.E. control | about 5–6 |
| Temperature of cooking | about 104–107° C. |
| Temperature of dextrinization | Not less than about 93° C., preferably about 95–98° C., |
| Temperature during refining | Greater than about 76° C. |
| Final D.E. | about 10–13 |

Having thus described our invention we claim:

1. A process for producing a low D.E. starch hydrolyzate which comprises (1) liquefying non-waxy corn starch in the presence of an alpha amylase by heating at a temperature within the range of from about 104°–107° C., (2) maintaining the liquefied starch hydrolyzate of step (1) at a temperature above about 93° C. in the presence of alpha-amylase so as to dextrinize the hydrolyzate to a D.E. level within the range of from about 10–13, (3) terminating the reaction of step (2) by the addition of sufficient mineral acid to lower the pH of the dextrinized hydrolyzate to a level at which residual alpha-amylase is inactivated within the period of from about thirty to about sixty minutes while maintaining the hydrolyzate temperature at least above about 93° C., (4) refining the resulting hydrolyzate from step (3) while maintaining the hydrolyzate at a temperature of at least above about 76° C. during the refining operations, and (5) spray drying the refined hydrolyzate of step (4) so as to produce a dry free-flowing starch hydrolyzate.

2. The process of claim 1, wherein the pH of the starch hydrolyzate during step (2) is maintained within the range of from about pH 5 to about pH 6 and the temperature of the hydrolyzate is maitained in a range of from about 95° C. to about 98° C.

3. A process for producing a low D.E. starch hydrolyzate which comprises (1) liquefying non-waxy corn starch in the presence of an alpha-amylase by heating at a temperature within the range of from about 104°–107° C., (2) maintaining the liquefied starch hydrolyzate of step (1) at a temperature above about 93° C. in the presence of alpha-amylase so as to dextrinize the hydrolyzate to a D.E. level within the range of from about 10–13, (3) terminating the reaction of step (2) by the addition of sufficient mineral acid to lower the pH of the dextrinized hydrolyzate to a level at which residual alpha-amylase is inactivated within the period of from about thirty to about sixty minutes while maintaining the hydrolyzate temperature at least above about 93° C., (4) refining the resulting hydrolyzate from step (3) by treatment with activated carbon while maintaining the hydrolyzate at a temperature of at least above about 76° C., (5) removing the activated carbon by filtration while maintaining the hydrolyzate at a temperature of at least above about 76° C., (6) evaporating the hydrolyzate filtrate of step (5) while maintaining the hydrolyzate at a temperature of at least above about 76° C. to a dry solids content such that permits the hydrolyzate to be spray dried, and (7) spray drying the hydrolyzate so as to produce a dry free-flowing starch hydrolyzate.

* * * * *